United States Patent [19]
Backlund et al.

[11] Patent Number: 6,004,580
[45] Date of Patent: Dec. 21, 1999

[54] PHARMACEUTICAL COMPOSITIONS DERIVED FROM MICROEMULSION-BASED GELS

[75] Inventors: Sune Backlund, Pargas; Folke Eriksson, Karis; Maria Rantala, Merimasku; Pertti Rantala, Littoinen; Kari Varho, Naantali, all of Finland

[73] Assignee: Leiras Oy, Turku, Finland

[21] Appl. No.: 08/727,545

[22] PCT Filed: Apr. 28, 1995

[86] PCT No.: PCT/FI95/00234

§ 371 Date: Nov. 12, 1997

§ 102(e) Date: Nov. 12, 1997

[87] PCT Pub. No.: WO95/31969

PCT Pub. Date: Nov. 30, 1995

[30] Foreign Application Priority Data

May 24, 1994 [FI] Finland ..................................... 942387

[51] Int. Cl.⁶ ............................ A61K 9/66; A61K 9/127; A61K 9/64
[52] U.S. Cl. .......................... 424/450; 424/455; 424/456; 424/460; 424/461; 514/937; 514/938; 514/944
[58] Field of Search ..................................... 424/450, 455, 424/456, 457, 460, 461; 514/937, 938, 944

[56] References Cited

U.S. PATENT DOCUMENTS

| | | | |
|---|---|---|---|
| 4,619,926 | 10/1986 | Eckert | 514/210 |
| 5,206,219 | 4/1993 | Desai | 514/3 |
| 5,294,249 | 3/1994 | Luisi | 106/130 |
| 5,342,625 | 8/1994 | Hauer et al. | 424/455 |

FOREIGN PATENT DOCUMENTS

| | | |
|---|---|---|
| 2 222 770 | 3/1990 | United Kingdom . |
| WO 86/02264 | 4/1986 | WIPO . |

OTHER PUBLICATIONS

P. L. Luisi et al. "Organogels from water–in–oil microemulsions", Colloid and Polymer Science. 268: 356–374, 1990.

P.L. Luisi et al., "Organogels From Water–in–oil Microemulsions", 268 *Colloid & Polymer Science* 356–374 (1990).

*Primary Examiner*—Thurman K. Page
*Assistant Examiner*—Lakshmi Channavajjala
*Attorney, Agent, or Firm*—Lydon & Brown, LLP

[57] ABSTRACT

A pharmaceutical composition containing a microemulsion made up of a hydrophilic component, a lipophilic component, a surfactant and a drug, where the hydrophilic component, the lipophilic component and the surfactant form, when examined on a macroscopic scale, a one-phase solution. The hydrophilic component is dispersed as colloidal droplets in the lipophilic component, or the lipophilic component is dispersed as colloidal droplets in the hydrophilic component. According to still another alternative, the hydrophilic and the lipophilic components form a microemulsion with bicontinuous structure where the components form elongated adjacent channels. The drug is dissolved in the dispersed component or, in the case of a microemulsion with bicontinuous structure, in the hydrophilic or the lipophilic component. The microemulsion is stabilized by means of the surfactant. It is characteristic that a gelatinizer and water are added to the microemulsion thereby bringing the microemulsion into a gel form.

15 Claims, 5 Drawing Sheets

PHARMACEUTICAL COMPOSITIONS DERIVED FROM MICROEMULSION-BASED GELS

This application is a continuation of a 371 of PCT/FI95/00234, filed Apr. 28,1995.

The invention relates to pharmaceutical compositions derived from microemulsion-based gels and method for their preparation. The invention further relates to gels as such based on o/w type microemulsions or microemulsions of bicontinuous structure.

Since the year 1990 water soluble enzymes have been immobilized in microemulsion-based gels (G D Rees, Thesis, University of East Anglia, (1990); G D Rees et al., Biochim Biophys Acta, 1073, (1991), 493; G D Rees & B H Robinson, Advanced Materials 5, (1993), 608; G D Rees et al., Indian J Chem, 32B, (1993), 30). The microemulsions used are of a water-in-oil type (w/o or "water in oil") in which the enzyme is dissolved in'water droplets surrounded by oil. For the stabilization of these microemulsions only surfactant AOT, which will be presented in greater detail later, has been used. Due to addition of gelatine and water the microemulsion is brought into a suitable form which can be added into the reaction vessel and, after the reaction has finished, removed therefrom. Hence the enzymes in a microemulsion-based gels are again available for use in the next reaction. However, these gels can be used only in organic solvents.

This invention relates to employment of said microemulsion gel technique as dosage forms of drugs, in particular systemic, like oral dosage forms. Depending on whether the drug is lipo-soluble or water soluble, a microemulsion which is of an oil-in-water type (o/w, "oil in water") or a water-in-oil-type (w/o, "water in oil") or a microemulsion with a so-called bicontinuous structure is used. The concept bicontinuous structure will be considered in greater detail later.

So far no workable pharmaceutical preparation has been presented in which the drug is immobilized in a microemulsion-based gel.

BACKGROUND

MICROEMULSIONS

Due to their excellent dissolution properties microemulsions have been increasingly used in various technological fields. They are used, for instance as detergents, in oil recovery and as the reaction environment of enzyme catalysts.

Microemulsions are also used as dosage forms of drugs. The British patent publications GB 2222770, 2228198 and 2257395 describe microemulsion concentrates containing cyclosporin which form o/w type microemulsions after addition of water.

Microemulsion denotes a thermodynamically stable and optically isotropic solution which consists of water (or more generally hydrophilic component), oil (or more generally lipophilic component) and surfactant which denotes a surface active substance with an amphilic character. Microemulsions are macroscopically, e.g. when observed visually, homogeneous one-phase solutions. However, if observed on microscopic level, it is noted that they are most heterogeneous. Microemulsions are composed of microscopic continuous domains of water or oil which are separated from one another by a monomolecular layer of the surfactant. The role of surfactant is stabilization of the microemulsion, for instance through decreasing interfacial tension. The microemulsion is of an oil-in-water type (o/w, "oil in water"); a water-in-oil type (w/o, "water in oil") or has a bicontinuous structure (will be explained in more detail later).

The monomeric solubility of the surfactant both in water (hydrophilic component) and in oil (lipophilic component) must be low so that the surfactant could form a microemulsion with the highest possible stability.

The surfactant may be ionic or non-ionic. If the surfactant is ionic, it must have two hydrocarbon chains to form a microemulsion. If the ionic surfactant does not have two hydrocarbon chains, a neutral inorganic salt and a co-surfactant must be added. A short-chain alcohol is often used as the co-surfactant. When a two-chained ionic or a non-ionic surfactant is used, the microemulsion may be formed without any additives. In case the surfactant is too lipophilic to form spontaneously microemulsions in water, a component like ethanol may be added which reduces hydrophilicity of water. Due to its high solubility in water, ethanol is not considered to take part in the formation of a stabilizing interface but to remain in water. Hence it is often called as co-solvent.

FIG. 1 shows the phase diagram of an idealized oil-water-surfactant model system (Kemia-Kemi Vol. 20 (1993) 197). The phase diagram exhibits, in addition to two-phase (W I and W II) and three-phase (W-III) regions, a wide one-phase region (W IV), in which the microemulsions appear. On examining the phase diagram one finds from a region near the water corner an o/w type microemulsion in which there are oil droplets surrounded by the surfactant in water. In a corresponding way, in a region near the oil corner, a w/o type microemulsion is formed. Between these two regions is a region in which the structure of the microemulsion is bicontinuous. It is possible to solubilize water soluble or liposoluble materials, especially macromolecules or parts thereof which have amphilic properties, into water droplets or oil droplets or into bicontinuous structures.

GELATINATION AND GELS

By gelatinizing or gel formation is traditionally meant formation of a colloidal suspension in which the dispersed particles (lyophilic sol) partly coagulate so that a gel is formed. The particles in a lyophilic sol are stable because they are solvated. The gel formed is a threadlike mass containing a major part of the solvent. The final result is a pseudosolid or jelly-like product. One gelatination agent generally used is gelatin which is a naturally occuring polypeptide. Gelatin is insoluble in cold water but in warm water it dissolves and gelatinizes upon cooling the solution. When the solution is warmed, the gel reverts into a sol, i.e. the gel formation is reversible.

MICROEMULSION-BASED GELS

Gels denote soft, solid or pseudosolid systems comprising of two or more components one of which is a liquid constituting a major part (K Almdal et al., Polymer Gels and Networks 1 (1993) 5–17). The mutual gel formation of gelatin and microemulsion was first described in the literature in 1986 (Haering G & Luisi P L, J Phys Chem 90:5892 (1986); Quellet G & Eicke HF, Chimica 40:233 (1986)). The microemulsion in question was a w/o type microemulsion of water, isooctane and a sodium 1,4-bis (2-ethylhexyl) sulfosuccinate, which is generally called AOT. When small amounts of gelatin is added to this w/o microemulsion, the gelatin chains are enclosed into colloidal water droplets while part of the hydrophobic side chains of the gelatin chains adsorbs on the interface of the water droplet. Here gelatin acts as a co-surfactant. These gelatin-water droplets are 20–80 nm in size. At this stage the system forms a sol in which droplets appear as single colloidal particles as shown in FIG. 2A. However, attractive forces exist between the droplets. When an aqueous solution of gelatin is added or temperature is decreased, the sol changes into an electrically conductive cross-linked network of water droplets or a gel, shown in FIG. 2B. The transformation from sol into gel takes place in a very narrow temperature and water-gelatine concentration range. The change is reflected in viscosity, electrical conductivity and optical rotation. These microemulsion-based gels, like pure microemulsions, have different phase behaviour depending on their composition and behaviour (Quellet G & Eicke HF, Chimica 40:233 (1986)).

The literature further discloses other types of gels, i.e. lecithin gels (Scartazzini R & Luisi P L, J Phys Chem 92:829 (1988); Luisi P L et al., Colloid Polymer Science 268 (1990) 356) which are called organogels. These gels are not, however, formed by gelatination of microemulsions by a separate gelatinizer. These gels are formed simply by adding a very small amount of water into a solution of an organic solvent and lecithin.

The above gels based on w/o type microemulsions are suitable for various technical applications like immobilization of enzymes and as membranes in separation processes. Due to the toxicity of the AOT surfactants, the microemulsion-based gels described in the literature cannot be used as carriers for drugs, especially not for oral and other systemic pharmaceutical preparations. In patent publication WO 86/02264, the year of application being 1985, the inventor Luisi P L suggests an idea that w/o type microemulsions brought into a gel form could be applied as a pharmaceutical carrier and mentions that the AOT surfactant could be replaced with another surfactant. However, there are presented no examples of microemulsion-based gels based on other surfactants than AOT. In his article several years later (P L Luisi et al., Colloid Polymer Sci. 268 356–374 (1990)) the authors state at the end of the article that application of microemulsion-based gels in the field of cosmetics and pharmaceutics is problematic because AOT and organic solvents used would have to be substituted with pharmaceutically acceptable alternatives. It is further emphasized that it is not yet clear to what extend substitution of AOT is possible.

THE INVENTION

Thus it can be concluded that according to the literature it has not been possible to produce acceptable pharmaceutical preparations from w/o microemulsion-based gels known per se.

Such microemulsion-based gels that are based on o/w type microemulsions or microemulsions with bicontinuous structures have not at all been described in literature.

GENERAL DESCRIPTION OF THE INVENTION

This invention thus relates to a pharmaceutical composition derived from a microemulsion-based gel with an o/w-, w/o-, or bicontinuous structure and a method for its preparation. The invention further relates to gels as such that are based on o/w-type microemulsions or microemulsions of bicontinuous structure. These novel microemulsion-based gels can be used for immobilization of any substance provided that said substance dissolves in the hydrophilic or lipophilic part of the microemulsion.

The pharmaceutical composition according to the invention comprises a microemulsion made up of a hydrophilic component, a lipophilic component, a surfactant and a drug, wherein the hydrophilic component, lipophilic component and surfactant form, when examined on a macroscopic scale, a one-phase solution. In this kind of microemulsion 1) the hydrophilic component is dispersed as colloidal droplets in the lipophilic component, or 2) the lipophilic component is dispersed as colloidal droplets in the hydrophilic component, or 3) the hydrophilic and the lipophilic component form a microemulsion with bicontinuous structure wherein said components form elongated adjacent channels. The drug is dissolved in the dispersed component or in the hydrophilic or the lipophilic component of the bicontinuous microemulsion. The microemulsion is stabilized by means of the surfactant. It is characteristic that a gelatinizer and water is added to the microemulsion thereby bringing the microemulsion into a gel form.

The above wording "when examined on a macroscopic scale a one-phase solution", which also appears in the claims, denotes that the "solution", which is not an ideal solution, is thermodynamically stable and optically isotropic. The droplet size is typically in the size range 1–100 nm. When examined on a microscopic scale (e.g by an electron microscope or light scattering), the heterogeneous structure of said "solution" shows up.

Figure 1:
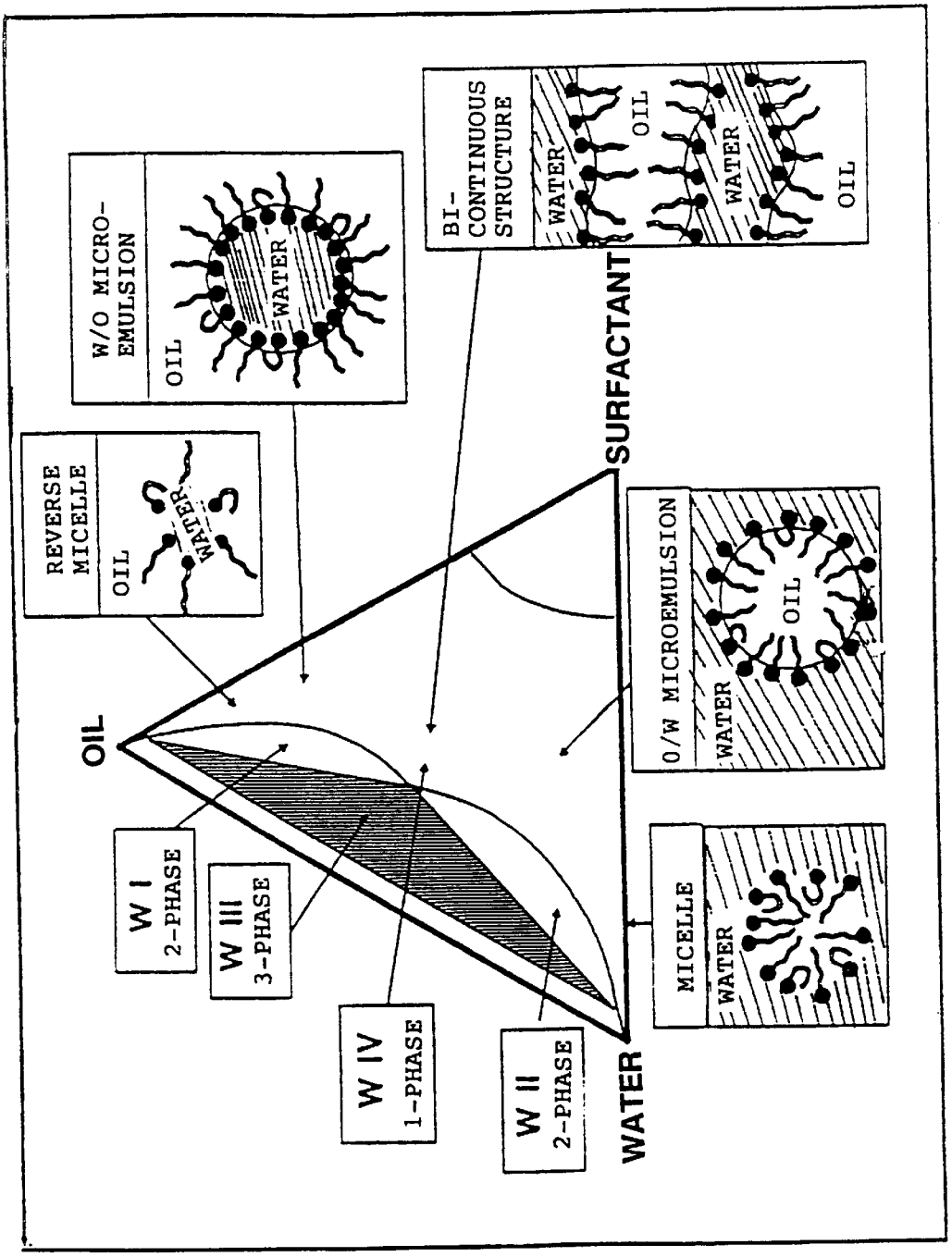
FIG. 1 illustrates microemulsion regions, micelle regions and reverse micelle regions of the composition of the present invention.
Figure 2A:
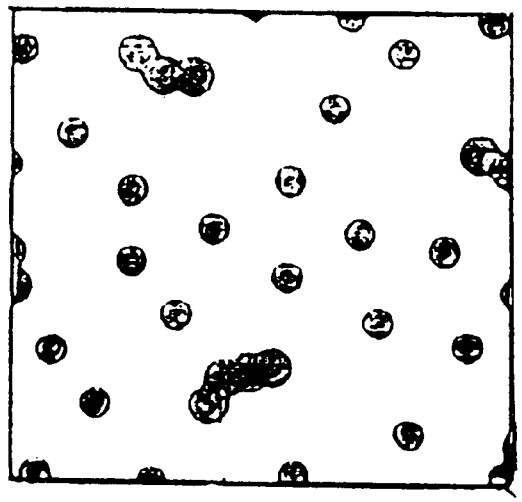
FIG. 2A shows droplets of a microemulsion of water, isooctane, sodium 1,4-bis(2-ethylhexyl)sulfosuccinate and gelatin which appear as single colloidal particles.
Figure 2B:
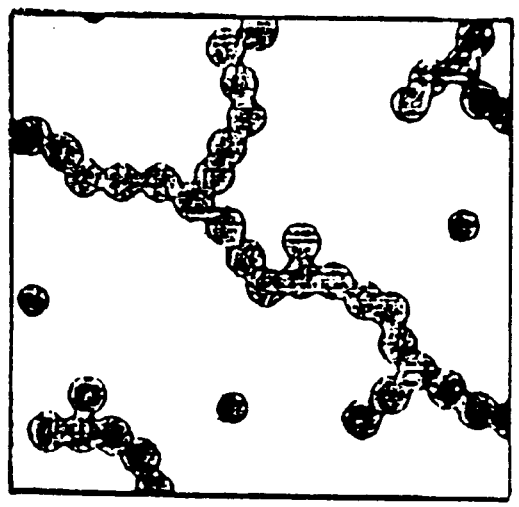
FIG. 2B depicts an electrically conductive, crosslinked network of water droplets, formed when an aqueous solution of gelatin is added to the microemulsion shown in FIG. 2A.

The term "microemulsion" as used in the definition of this invention in the description part and in the claims comprises both conventional microemulsion regions and micellar (micelles and-reverse micelles) regions as shown in FIG. 1.

The term "droplet" as used in the definition of this invention in the description part and in the claims comprises both a conventional microemulsion and micelle, reverse micelle, respectively.

According to one preferred embodiment, the pharmaceutical composition is based on such a gelatinized microemulsion in which the lipophilic component is dispersed as droplets in the hydrophilic component.

Particularly preferred is such a composition in which the hydrophilic component is water or a mixture of water and a pharmaceutically acceptable alcohol, and the lipophilic component is a pharmaceutically acceptable hydrocarbon, fatty acid, a mono-, di- or triglyceride of a fatty acid or mixtures thereof.

As suitable lipophilic components that are pharmaceutically acceptable can be mentioned paraffin oil which is a mixture of hydrocarbons or animal or vegetable oils with one or more $C_{8-20}$ fatty acid or a mono-, di- or triglyceride of a fatty acid. Examples of suitable fatty acid based oils are fish oil, cod-liver oil, castor oil, soybean oil, maize oil, olive oil, almond oil, peanut oil, peach oil, palm oil, coconut oil, rape oil or sunflower oil. These kinds of oils are mixtures of several unsaturated and saturated esterified fatty acids. Castor oil has proved to be particularly suitable, the main component (87%) being castor oil acid, a hydroxy substituted acid with the formula

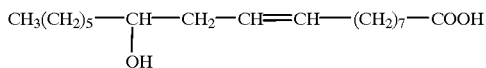

Other fatty acids of castor oil are oleic acid (7%), linoleic acid (3%), palmitinic acid (2%) and stearic acid (1%). The excellent microemulsion and solvent properties of the castor oil are probably due to the high hydroxy acid concentration. This leads to the assumption that also other natural or synthetic, pharmaceutically acceptable hydroxy substituted fatty acids with intermediate chain length are suitable as the lipophilic component or as a part thereof.

Pharmaceutically acceptable surfactants are ionic or non-ionic surface active materials. Particularly suitable surfactants are e.g. phospholipids, especially naturally occuring egg and soyabean lecithins. Besides these any other pharmaceutically acceptable surfactant can be naturally used like the surfactants known under the trade names Tween, Crempophor, Nikkol, Myrj, Cetiol etc.

Phospholipids, especially naturally occuring egg or soya-bean lecithins represent important surfactants. Lecithin is highly lipophilic due to two hydrocarbon chains but at the same time it is also hydrophilic due to polar zwitterionic head group. In water lecithins have a strong tendency to form lamellar liquid crystals at high lecithin contents. In water-oil systems lecithin is slightly too lipophilic to form a stable microemulsion. By adding a lower alcohol to the water the hydrophilic component is made less hydrophilic and in a system like this lecithin gives stable microemulsions. Alcohol acts as an amphilic co-solvent.

Suitable gelatinizers are e.g. gelatin or polysaccharides like agarose, agar, pectin or carrageen.

The pharmaceutical compositions according to the invention are suitable as carriers for both water soluble and lipo-soluble drugs. If the microemulsion is of the w/o type, the composition suits as carrier for water soluble drugs whereas gels based on o/w type microemulsions suit for immobilization of lipo-soluble drugs. If the microemulsion has a bicontinuous structure, the composition suits as carrier for both water soluble and lipo-soluble drugs.

In particular the gels according to the invention based on o/w microemulsions suit as carriers for cyclosporin, lipo-soluble vitamins or a steroid like e.g. hydrocortisone. Cyclosporins are cyclic polypeptides with a strong immunosuppressive effect. The body is formed by a ring structure of 11 amino acids

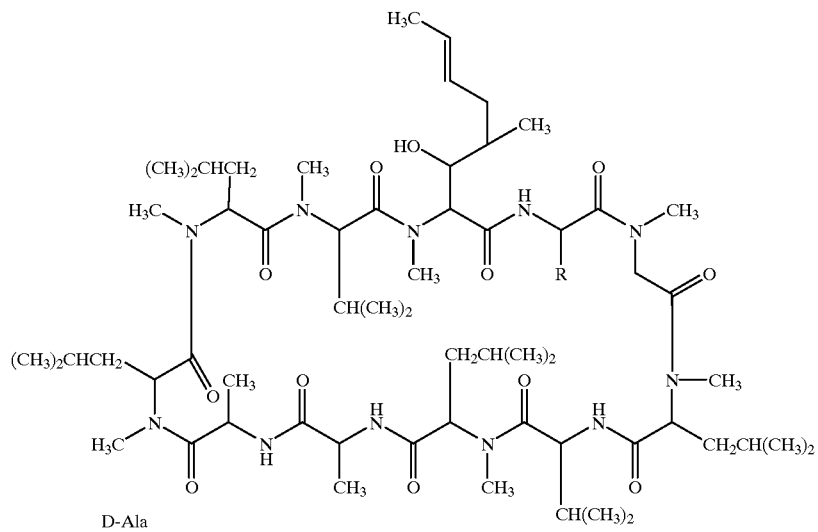

in which the substituent R may vary. An important commercial drug is cyclosporin or cyclosporin A in which R is ethyl. Other cyclosporins are cyclosporin B (R=methyl), cyclosporin C (R=—CH(OH)—CH$_3$), cyclosporin D (R=isopropyl), and cyclosporin G (R=1-propyl).

The obtained microemulsion-based gel is moulded into pieces of desired size and shape. The gel can be used as such for oral, rectal, intravaginal, transdermal or topical pharmaceutical preparations without any additives besides possible preserving agents.

All lipophilic materials, hydrophilic materials and surfactants do not together form a one-phase region of the kind described above which is the prerequisite for a microemulsion. Only those combinations which form one or more one-phase regions in the phase diagram are useful for the purpose of this invention. A further prerequisite for a successful pharmaceutical combination is that the drug can be incorporated into the microemulsion and does not break the structure of the microemulsion. Through testing only it is possible to definitely find out which component combinations yield the desired final result.

This invention also relates to a method for the preparation of a pharmaceutical composition based on a microemulsion-based gel. It is characteristic that a hydrophilic component, a lipophilic component and a surfactant are mixed into a one-phase microemulsion and a drug is added to the microemulsion and a gelatinizer is dissolved in water at a raised temperature and the microemulsion containing the drug is added thereto.

The pharmaceutical compositions derived from microemulsion-based gels are manufactured essentially in the following way. When a certain surfactant and a lipophilic component have been selected, at least a partial phase diagram should be created in order to show the liquid phases. A phase diagram for a particular system is usually created by weighing each component separately in a test tube. Different compositions of the system can then be analyzed visually after they have stabilized at 25° C. for twenty-four hours. The most important compositions with respect to gelatinizing are one-phase solutions (microemulsions). As stated above they are either water/oil, oil/water or bicontinuous microemulsions. Such a specific composition is then warmed to 45° C. at which temperature the drug is added. After this the microemulsion containing the drug is mixed with a 40% gelatin-water mixture at about 50–55° C. Mixing is continued until the solution is homogeneous. Upon lowering the temperature the solution changes pseudosolid. If lecithin is used as the surfactant, it does not, however, become quite transparent but has a yellow thick colour due to lecithin.

The structure of microemulsions (water/oil, oil/water or bicontinuous) can be determined by means of published methods e.g. NMR, electron microscope, or electrical conductivity (K Shinoda et al., Langmuir 9 (1993) 1254; K Shinoda et al., J Phys Chem 95 (1991) 989–993; J Eastoe et al., Advances Colloid Interface Sci. 36 (1991) 1–31).

This invention relates further to a novel gelatinous microemulsion which is characterized in that it comprises a lipophilic component which is dispersed as colloidal droplets in a hydrophilic component, or that a hydrophilic and a lipophilic component form a microemulsion with a bicontinuous structure wherein said components form elongated intertwined channels.

Such a novel microemulsion-based gel suits well as carrier not only for drugs but also for other substances. Application of this microemulsion-based gel as the carrier of some substance in general belongs also to the scope of this invention.

EXPERIMENTS

The invention will be explained in more detail in the following by means of examples.

EXAMPLE 1

The phase diagram of the system soya lecithin-hexadecane-water/ethanol.

Figure 3:
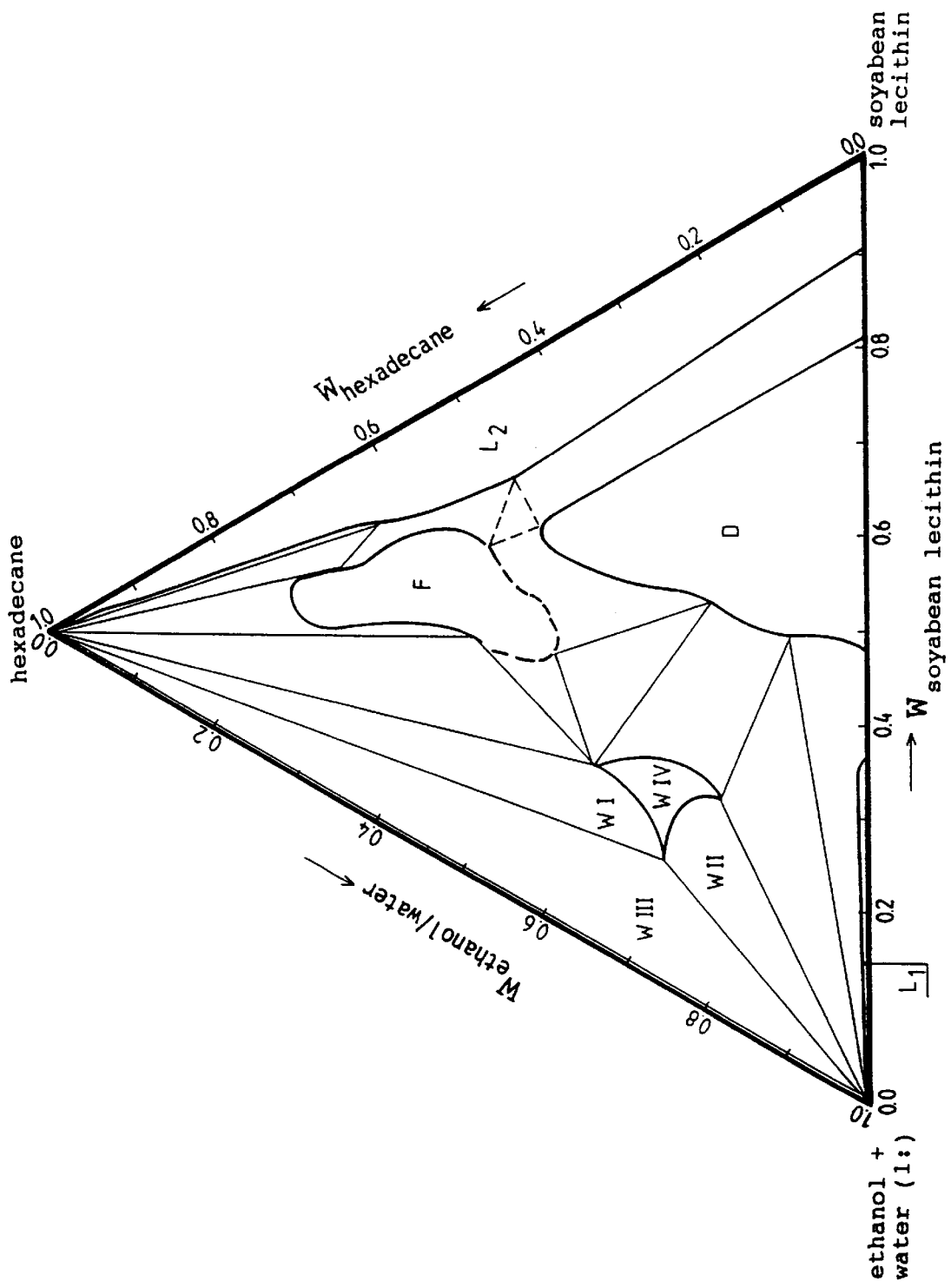
FIG. 3 illustrates the phase diagram of a soya lecithin-hexadecane-water/ethanol system.

The water/ethanol solution used contained 50 weight-% ethanol. The components of each concentration combination were weighed separately in a test tube. After 24 hour stabilization at a temperature of 25° C. the phases were visually analyzed between polarized glasses. The obtained phase diagram is shown in FIG. 3. The figure shows that a one-phase region (W IV) had been found by visual observation. In FIG. 3 $L_1$ denotes a micellar region and $L_2$ a region of reverse micelles. F and D denote liquid crystal phases which are anisotropic systems.

EXAMPLE 2

The phase diagram of the system egg lecithin-paraffin oil-water/ethanol.

The water/ethanol solution used contained 80 weight-% ethanol. The phase diagram was produced according to the previous example. As seen in the phase diagram (FIG. 4) a one-phase system was found also in this system but it required a much higher ethanol and lecithin concentration than in Example 1. The micellar region is indicated by $L_1$ and $L_2$.

EXAMPLE 3

The phase diagram of the system soyabean lecithin-paraffin oil-water/ethanol.

The water/ethanol solution used contained 50 weight-% ethanol. The phase diagram was produced as in Example 1. The phase diagram (FIG. 5) shows that a one-phase (1 Φ) region exists near the corner of the hydrophilic component (water/ethanol). The $L_1$ region is very small and does appear in the figure.

EXAMPLE 4

A microemulsion-based gel containing cyclosporin (microemulsion: soyabean lecithin-paraffin oil-water/ethanol)

Test a

Figure 5:
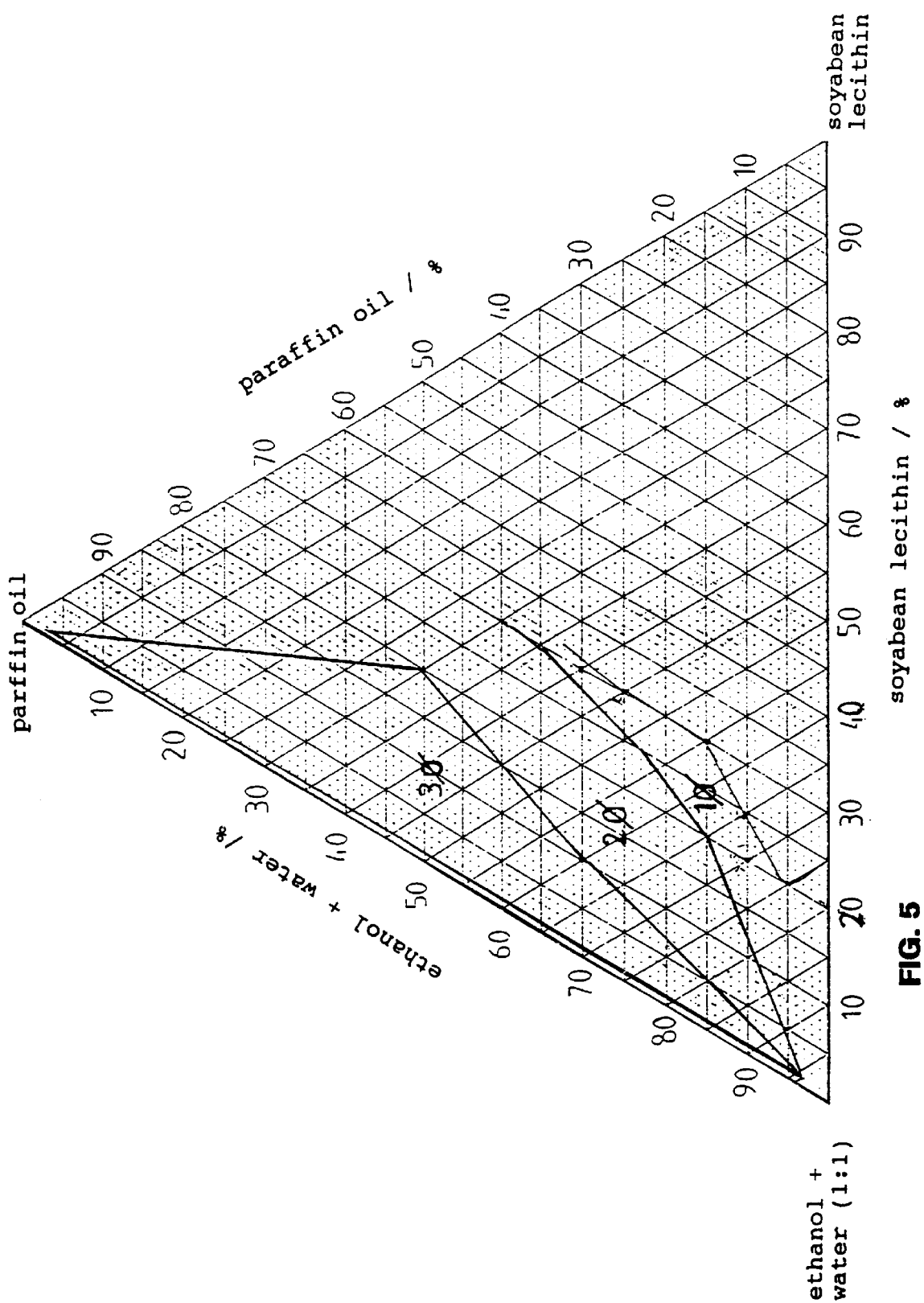
FIG. 5 depicts the phase diagram of an soyabean lecithin-paraffin oil-water/ethanol system.

On the basis of the phase diagram of FIG. 5 a microemulsion was prepared that contained 0.9065 g soya lecithin, 1.5855 g ethanol, 1.5855 g water, and 0.453 g paraffin oil (lecithin 20%, paraffin oil 10% and water/ethanol 70%). An amount of 0.2 g of cyclosporin, which dissolved well, was added to the microemulsion. An amount of 1.4 g of gelatin (Bloom 300) was dissolved in 2.06 g of water, the temperature of which was 55° C.

Two additional tests b) and c) were made according to the above test a) using the same components but in different amounts.

The compositions of the pharmaceutical preparations derived from microemulsion-based gels were as follows (the amounts in %):

|  | a | b | c |
| --- | --- | --- | --- |
| lecithin | 11.1 | 5.5 | 8.3 |
| paraffin oil | 5.5 | 2.8 | 4.2 |
| ethanol | 19.4 | 23.5 | 21.4 |
| water | 44.5 | 48.7 | 46.6 |
| gelatin | 17.1 | 17.1 | 17.1 |
| ciclosporin | 2.4 | 2.4 | 2.4 |

The electrical conductivity of i) the microemulsion, ii) the microemulsion containing cyclosporin, and iii) the microemulsion based gel containing cyclosporin were measured. The conductivity of the gel was higher than that of the microemulsions.

EXAMPLE 5

A microemulsion-based gel containing cyclosporin with castor oil as the lipophilic component.

A microemulsion-based gel containing cyclosporin was prepared in the manner described above with the exception that castor oil was used instead of paraffin oil. A one-phase region was found already with a very small concentration (3%) of castor oil. In addition to castor oil the microemulsion contained 25% lecithin and 72% water/ethanol (1:1) solution. A gel with the following composition was prepared:

| | |
|---|---|
| lecithin | 13.0% |
| ethanol | 18.7% |
| water | 42.3% |
| castor oil | 1.5% |
| gelatin | 16.0% |
| ciclosporin | 8.5% |

The solubility of cyclosporin in the microemulsion was surprisingly high considering the small amount of castor oil. The solubility of cyclosporin in castor oil is 250 mg/ml but if cyclosporin in the above gel were dissolved solely in the castor oil component, a solubility value of 5200 mg cyclosporin per g of castor oil would be obtained. Ethanol/water seems to take part in the dissolution of cyclosporin.

EXAMPLE 6

A microemulsion-based gel containing vitamin A with paraffin oil as the lipophilic component.

The following composition was prepared:

| | |
|---|---|
| lecithin | 8.50% |
| ethanol | 21.97% |
| water | 47.59% |
| paraffin oil | 4.25% |
| vitamin A | 0.17% |
| gelatin | 17.25% |

EXAMPLE 7

Microemulsion-based gels containing vitamin E, D or A with castor oil as the lipophilic component.

Following compositions were prepared:

Composition with vitamin E:

| | |
|---|---|
| lecithin | 14.17% |
| ethanol | 20.40% |
| water | 45.37% |
| castor oil | 1.70% |
| vitamin E | 0.85% |
| gelatin | 17.51% |

Composition with vitamin D:

| | |
|---|---|
| lecithin | 14.18% |
| ethanol | 20.41% |
| water | 46.18% |
| castor oil | 1.71% |
| vitamin D | 0.0012% |
| gelatin | 17.52% |

Composition with vitamin A:

| | |
|---|---|
| lecithin | 14.18% |
| ethanol | 20.41% |
| water | 46.02% |
| castor oil | 1.70% |
| vitamin A | 0.17% |
| gelatin | 17.52% |

EXAMPLE 8

A microemulsion-based gel containing cyclosporin with agar as the gelatinizer.

The following composition was prepared:

| | |
|---|---|
| lecithin | 14.3% |
| ethanol | 20.6% |
| water | 54.6% |
| castor oil | 1.7% |
| ciclosporin | 5.0% |
| agar | 3.8% |

The advantage of agar over a gelatin gel is that agar is needed less than gelatin. Furthermore agar withstands better the raised temperature than a gelatin gel. Agar remained solid even at 50° C.

EXAMPLE 9

Microemulsion-based gels containing vitamin A or E with agar as the gelatinizer.

The following composition was prepared:

Composition with vitamin A:

| | |
|---|---|
| lecithin | 15.16% |
| ethanol | 21.83% |
| water | 57.80% |
| castor oil | 1.82% |
| vitamin A | 0.18% |
| agar | 3.21% |

Composition with vitamin E:

| | |
|---|---|
| lecithin | 15.16% |
| ethanol | 21.84% |
| water | 57.06% |
| castor oil | 1.82% |
| vitamin E | 0.90% |
| agar | 3.22% |

Figure 4:
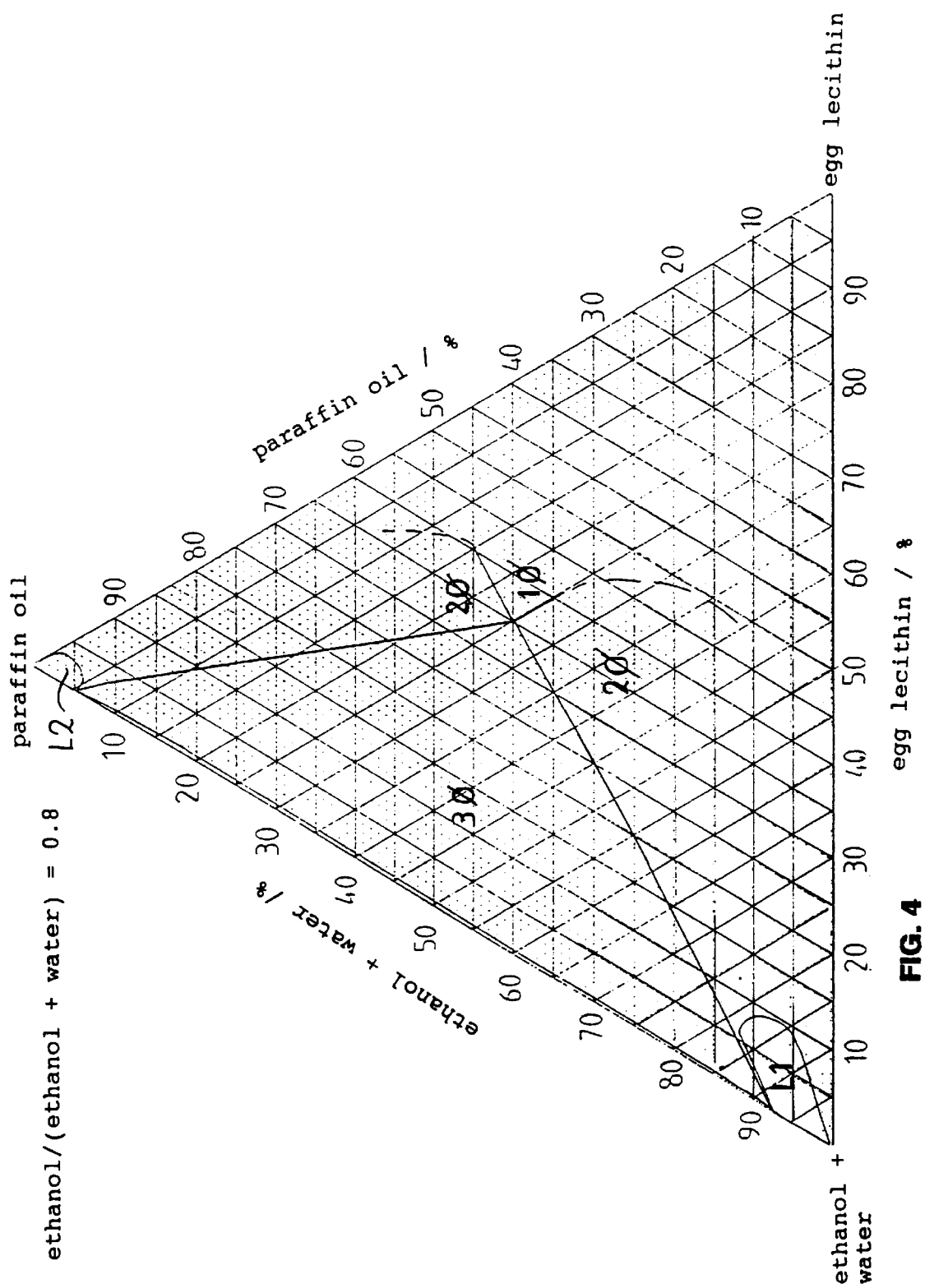
FIG. 4 shows the phase diagram of an egg lecithin-paraffin oil-water/ethanol system.

The phase diagrams shown in FIGS. 3–5 are valid at 25° C. without any drug added.

It is obvious to a specialist in the field that different embodiments of the invention may vary within the limits set forth in the enclosed claims.

We claim:

1. A pharmaceutical composition comprising a microemulsion made up of a hydrophilic component, a lipophilic component, a surfactant and a drug, wherein the hydrophilic component, the lipophilic component and the surfactant form, when examined on a macroscopic scale, a one-phase solution, wherein the lipophilic component is dispersed as colloidal droplets in the hydrophilic component, or the hydrophilic and the lipophilic components form a microemulsion with bicontinuous structure wherein said components form elongated intertwined channels, and the drug is dissolved in the dispersed component or in the hydrophilic or the lipophilic component of a microemulsion of bicontinuous structure, and the microemulsion is stabilized by means of the surfactant, wherein a gelatinizer and water are added to the microemulsion thereby bringing the microemulsion into gel form characterized in that the gelatinizer is gelatin or a polysaccharide and that the surfactant is a non-toxic, pharmaceutically acceptable component, and wherein said gel form is a reversible gel.

2. A pharmaceutical composition according to claim 1 characterized in that the lipophilic component of the microemulsion is dispersed as droplets in the hydrophilic component.

3. A pharmaceutical composition according to claim 1 characterized in that the hydrophilic component and the lipophilic component form a microemulsion with bicontinuous structure.

4. A pharmaceutical composition according to claim 1,2 or 3 characterized in that the hydrophilic component is water or a mixture of water and a pharmaceutically acceptable alcohol, and the lipophilic component is a pharmaceutically acceptable hydrocarbon, fatty acid, a mono-, di- or triglyceride of a fatty acid or mixtures thereof.

5. A pharmaceutical composition according to claim 4 characterized in that the lipophilic component is paraffin oil.

6. A pharmaceutical composition according to claim 4 characterized in that the lipophilic component contains one or more pharmaceutically acceptable $C_{8-20}$-fatty acid or a mono-, di- or triglyceride of a fatty acid.

7. A pharmaceutical composition according to claim 6 characterized in that the fatty acid is hydroxyl substituted.

8. A pharmaceutical composition according to claim 1 characterized in that the surfactant is a phospholipid.

9. A pharmaceutical composition according to claim 1 characterized in that the polysaccharide is agarose, agar, pectin or carrageen.

10. A pharmaceutical composition according to claim 1 characterized in that the drug is a cyclosporin, lipo-soluble vitamin or a steroid.

11. A pharmaceutical composition according to claim 10 characterized in that the drug is cyclosporin; the lipophilic component which is dispersed in the hydrophilic component is castor oil; the hydrophilic component is a water-ethanol solution and the surfactant is soybean lecithin.

12. A pharmaceutical composition according to claim 1 characterized in that the gel is sufficiently viscous to be shaped as such into separate pieces.

13. A method for the preparation of a pharmaceutical composition characterized in that a hydrophilic component, a lipophilic component and a non-toxic, pharmaceutically acceptable surfactant are mixed into a one-phase microemulsion, wherein the lipophilic component is dispersed as colloidal droplets in the hydrophilic component, or the hydrophilic and the lipophilic components form a microemulsion with bicontinuous structure wherein said components form elongated intertwined channels, and a drug is added to the microemulsion and a gelatinizer is dissolved in water at a raised temperature and the microemulsion containing the drug is added thereto.

14. A gelatinous microemulsion which comprises a hydrophilic component, a lipophilic component, a pharmaceutically acceptable surfactant and a gelatinizer, and which is used for immobilizing a substance, the microemulsion being stabilized by means of the surfactant and forming on a macroscopic scale a one-phase solution, the gelatinizer and water being added to the microemulsion thereby bringing the microemulsion in gel form, characterized in that the gelatinizer is gelatin or a polysaccharide, and the lipophilic component is dispersed as colloidal droplets in the hydrophilic component, or that the hydrophilic and the lipophilic components form a microemulsion of bicontinuous structure wherein said components form elongated intertwined channels.

15. A pharmaceutical composition according to claim 1 characterized in that the surfactant is lecithin.

* * * * *